United States Patent [19]

Mori

[11] Patent Number: 4,501,154

[45] Date of Patent: Feb. 26, 1985

[54] METHOD FOR MEASURING AN ADHESIVE STRENGTH OF A MULTI-LAYER MATERIAL

[75] Inventor: Sanae Mori, Nagoya, Japan

[73] Assignee: Daido Metal Company Ltd., Nagoya, Japan

[21] Appl. No.: 483,089

[22] Filed: Apr. 8, 1983

[30] Foreign Application Priority Data

Apr. 16, 1982 [JP] Japan ................................. 57-63702

[51] Int. Cl.$^3$ ............................................ G01N 19/04
[52] U.S. Cl. ........................................ 73/827; 73/856
[58] Field of Search ...................... 73/150 A, 827, 842, 73/856

[56] References Cited

U.S. PATENT DOCUMENTS 3,527,093 9/1970 Sellers ................................ 73/150 A
4,346,602 8/1982 Gould et al. ...................... 73/150 A

FOREIGN PATENT DOCUMENTS 29792 3/1977 Japan ..................................... 73/827

OTHER PUBLICATIONS

R. P. Anjard, "Thick Film Conductor Adhesion Testing", *Microelectronics and Reliability*, v. 10, (1971), pp. 269–275.

K. L. Mittal, "Adhesion Measurement of Thin Films," *Electrocomponent Science and Technology*, v. 3, No. 1, (Jun. 1976), pp. 21–42.

*Primary Examiner*—S. Clement Swisher
*Assistant Examiner*—John E. Chapman, Jr.
*Attorney, Agent, or Firm*—Karl W. Flocks; Sheridan Neimark

[57] ABSTRACT

A method for measuring an adhesive strength of a multi-layer material having at least two layers, such as a plain bearing, which method includes the steps of placing a mold on one surface of the multi-layer material, casting a brazing metal into the mold to form and secure a resulting cast structure to the one surface of the multi-layer material such that the cast structure includes a first column portion connected to and extending substantially upright from the one surface of the multi-layer, an intermediate portion extending and diverging in diameter from the upper end of the first column portion and a second column portion extending from the upper end of the intermediate portion, causing the opposite chucks of a tension tester to grasp the second column portion and the multi-layer material or a holder connected to the multi-layer material, respectively, and applying a tensile force to the respective layers of the multi-layer material in a direction transverse to the one surface of said multi-layer material.

3 Claims, 29 Drawing Figures 4,501,154

METHOD FOR MEASURING AN ADHESIVE STRENGTH OF A MULTI-LAYER MATERIAL

BACKGROUND OF THE INVENTION

The invention relates to a method for measuring an adhesive strength of a multilayer material having at least two layers such as a plain bearing, and more specifically to a method for measuring the adhesive strength of a copper or nickel or zinc plating layer on a steel back, or a copper or nickel or zinc strike plating layer on a bearing with an overlay, or an aluminum alloy or Kelmet alloy layer.

In the prior art, there have been proposed such measuring methods as the knife test, heat treatment blister test and folding test. However, such prior methods have involved the following disadvantages:

(1) It is impossible to measure adhesive strength quantitatively.

(2) Particular test pieces must be prepared separately from actual products for the measurement of adhesive strength.

SUMMARY OF THE INVENTION

It is an object of the invention to eliminate these disadvantages of the prior art.

It is another object of the invention to provide a simple method for correctly and rapidly giving quantitative measurement of the adhesive strength of a multilayer material.

In the method of the invention, test pieces directly available from actual products can be used, and accordingly it is not necessary to prepare any particular test pieces. Thus it is possible to measure an adhesive strength of a product itself rather than a dummy.

Briefly, the invention provides a method for measuring the adhesive strength of a multi-layer material, said method comprising placing a mold on one surface of said multi-layer material to be tested, casting a brazing metal into said mold to form and secure a resulting cast structure to said one surface of the multi-layer material, said structure including a first column portion connected to and extending substantially upright from the one surface, an intermediate portion diverging in diameter from the upper end of said first column portion and a second column portion extending from the upper end of said intermediate portion, causing chucks of a tension tester to grasp said second column portion of the cast structure and said multi-layer material or a holder connected to the material, and applying a tensile force to the respective layers of said multi-layer material along the vertical. The brazing metal as used in embodying the invention may include a soft solder such as a lead-tin alloy solder, zinc-tin alloy solder and the like, a hard solder such as a silver solder (for example, a silver-copper alloy with additions of cadmium and zinc and having a melting point of about 700° C.), gold solder, brass solder and the like, a lead-tin-bismuth solder having a low melting point, a lead-cadmium solder, a lead-silver solder, a cadmium-zinc solder and so on. A suitable brazing metal may be selected from these solders depending upon the magnitude of the adhesive strength of respective layers of a test piece to be measured.

DESCRIPTION OF THE PREFERRED EMBODIMENT

Figure 1:
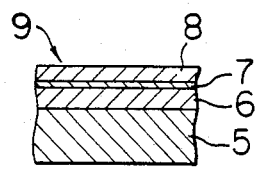
FIG. 1 is a fragmentary sectional view of a test piece of a plain bearing formed of a multi-layer material.

Referring to FIG. 1, there is shown in partial section a test piece of a multi-layer material to be measured. This test piece 9 serves as a plain bearing and consists of four layers, that is, a layer 5 of steel back (low carbon steel), a copper-lead alloy layer 6 composed of, for example, 28.0% to 32.0% of lead, less than 1.0% of tin, less than 2.0% of nickel or silver, less than 0.8% of iron, less than 1.0% of impurities and the remainder of copper, or composed of 23.0% to 27.0% of lead, less than 1.0% of tin, less than 2.0% of nickel or silver, less than 0.8% of iron, less than 1.0% of impurities and the remainder of copper, nickel plating layer 7 and a lead alloy surface layer 8 composed of, for example, 8.0% to 14.0% of tin and the remainder of lead, or of 8.0% to 14.0% of tin, 2.0% to 3.5% of copper and the remainder of lead.

Figure 2:
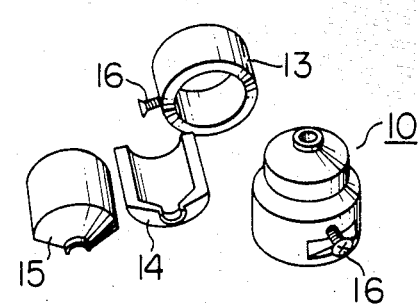
FIG. 2 is a perspective view of a mold for use in casting a brazing metal and its parts.

Degreasing (if necessary), preheating, polishing and coating of flux mixed with burnt borax, sodium carbonate, sodium chloride for removal of oxide and the like is applied on the lead alloy surface layer 8 of the test piece 9. Thereafter the mold as shown in FIG. 2 is positioned on the surface of the lead alloy surface layer 8. The mold 10 comprises halves 14 and 15, and a holder 13, and is assembled by securing the halves 14 and 15 to the holder 13 by means of a set screw 16 to have an upper opening of larger diameter and a lower opening of smaller diameter.

Figure 3:
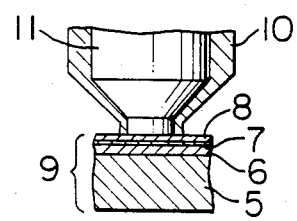
FIG. 3 is a sectional view showing the mold resting on the test piece of FIG. 1 to cast a brazing metal.
Figure 4:
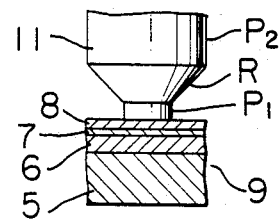
FIG. 4 is a sectional view similar to FIG. 3 except that the mold is removed.

The mold 10 is shown in FIG. 3 as being positioned on the surface of the lead alloy surface layer 8. It is preferable to preheat the mold 10 before placing the same on the surface of the layer 8. A heated, at 350° C., melted soft solder (composed of 70% of tin and 30% of lead) is poured into the mold 10, as having been preheated, through the upper opening of larger diameter to provide a cast structure 11. In FIG. 4, the mold 10 is removed, and the structure 11 comprises a first column portion $P_1$ connected to and extending upright from the surface layer 8, a frusto conical portion R diverging from the upper end of the first column portion and a second column portion $P_2$ extending from the upper end of the frustoconical portion R.

Figure 5:
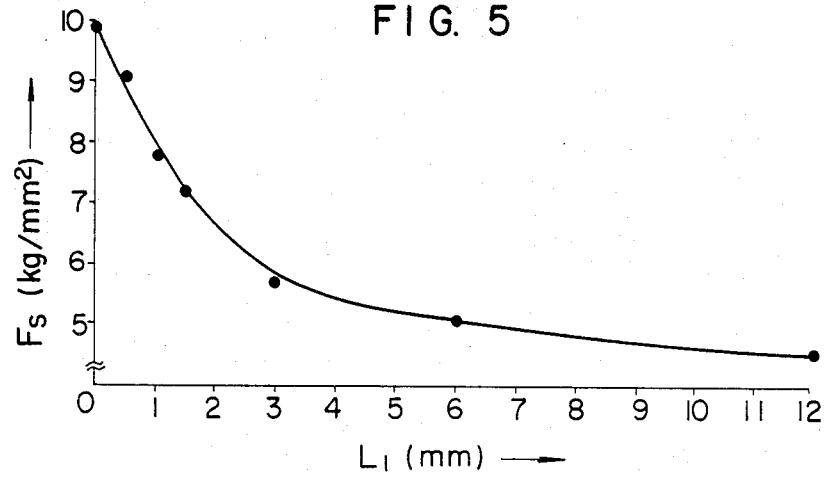
FIG. 5 is a graph showing the tensile strength of a first column portion of a cast structure relative to a length of the column portion.
Figure 6:
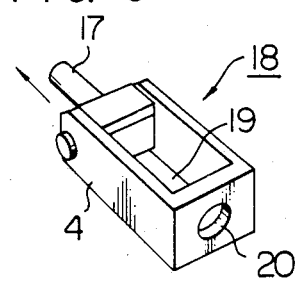
FIG. 6 is a perspective view of a holder serving as one of the grip members for the test piece.

The first column portion $P_1$ has a diameter of 8 mm and a height of 3 mm, and the second column portion $P_2$ has a diameter of 20 mm. These dimensions of the cast structure can be varied depending upon the size of the test piece, and are not limited to any particular dimensions. Thus after adhering the structure 11 to the surface layer 8 measurement of adhesive strength is effected by exerting a tensile force on the respective layers of the test piece in the vertical direction in such a manner that both the second column portion $P_2$ and the test piece are grasped by opposite chucks of a tension tester. When the thickness of the test piece 9 is large, the piece itself can be grasped directly by the chuck of the tension tester. When the thickness of the test piece is small, it is advantageous to use a holder 18 which, as shown in FIG. 6, comprises a grip portion 17 and a U-shaped frame member 4 having leg portions 19 and formed with an opening 20. By placing the test piece 9 between the leg portions 19 of the frame member 4 with the second column portion $P_2$ of the structure 11 inserted through the opening 20 of the frame member 4, tensile force produced by the tension tester can be applied between the second column portion $P_2$ of the structure 11 and the grip portion 17 of the holder 18. FIG. 5 illustrates a relationship between the length $L_1$ (mm) of the first column portion $P_1$ of the cast structure 11 and a tensile strength (kg/mm$^2$) of the first column portion $P_1$ when solder composed of 70% of tin and 30% of lead was used. As seen from the drawing, the tensile strength of the first column portion $P_1$ is reduced as the length thereof becomes large. When the adhesive strength of the test piece 9 is large, the first column portion would be broken and make measurement impossible unless the length of the first column portion were small. In this regard, the length $L_1$ of the column portion is selected depending upon the magnitude of the adhesive strength of the test piece 9 and the strength of solder.

Figure 9:
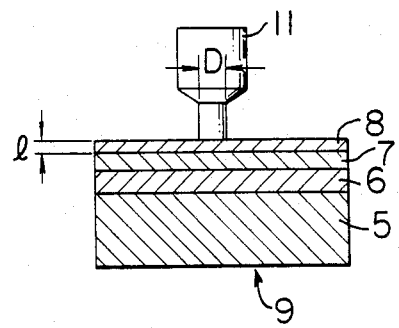
FIG. 9 is a partially sectonal view showing a thick testing piece adapted to undergo tension test making no use of any holder.
Figure 11:
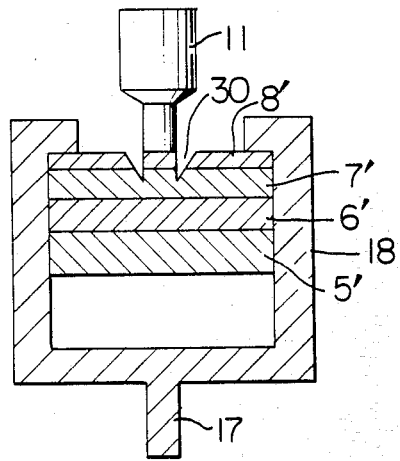
FIG. 11 is a partially sectional view showing how adhesive force is accurately measured between a thick surface layer and a layer immediately therebelow.
Figure 12:
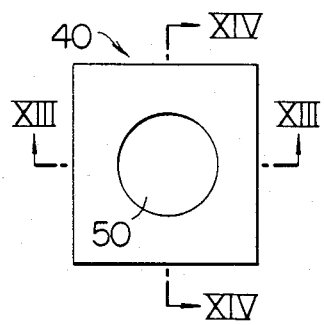
FIG. 12 is a plan view showing a supplementary tool.
Figure 13:
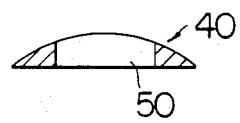
FIG. 13 is a sectional view taken along the line XIII—XIII in FIG. 12.
Figure 14:
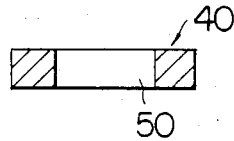
FIG. 14 is a sectional view taken along the line XIV—XIV in FIG. 12.
Figure 15:
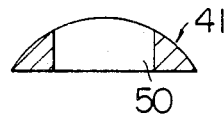
FIGS. 15 to 17 are sectional views showing supplementary tools having different curvatures from that of the supplementary tool of FIG. 12.
Figure 16:
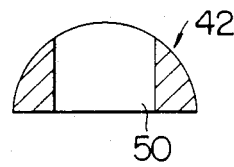
Figure 17:
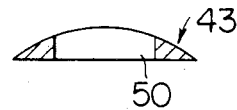

Referring now to FIG. 9, there is shown a test piece 9 having a large thickness which is used to be grasped by the tension tester in measurement. Assuming that a first column portion of the cast structure 11 has a diameter of 8 mm and a lead alloy surface layer 8 is an overlay having a thickness of 50 micron, an area conducive to adhesive strength is represented by $\pi \times (8/2)^2 = 50.24$ mm$^2$, and an area conducive to shearing strength is represented by $2\pi \times (8/2) \times 0.050 = 1.256$ mm$^2$, so that the latter is about one fortieth of the former. Thus any notch portion 30 as shown in FIG. 11 is not required to be provided in the test piece 9 of FIG. 9. When the assembly as shown in FIG. 9 is subjected to tension testing, the weakest portion of the layers 8, 7 and 6 will be broken.

Figure 10:
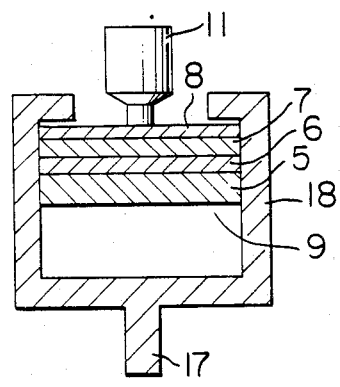
FIG. 10 is a partially sectional view showing a thin test piece adapted to undergo tension testing making use of a holder.

In FIG. 10, there is shown a test piece 9 having a small thickness and combined with a holder 18. In case the thickness of a lead alloy surface layer 8 is less than 0.1 mm, measurement of adhesive strength can be performed without the need of any notch portion 30 such as shown in FIG. 11.

FIG. 11 shows an assembly of a cast structure 11 and a test piece 9 engaged by a holder 17 and including a lead alloy surface layer 8'. In the assembly, a notch portion 30 is formed circumferentially along the periphery of a first column portion of the cast structure 11 to extend into the layers 8' and 7'. The notched portion 30 is formed by cutting the layers by means of a knife. The provision of such notch portion enables correct measurement of an adhesive strength between the layers 8' and 7'.

The method as described above enables quantitatively measuring adhesive strength of multi-layer materials. Adhesive strength can be determined by measuring tensile strength of the materials.

Figure 7:
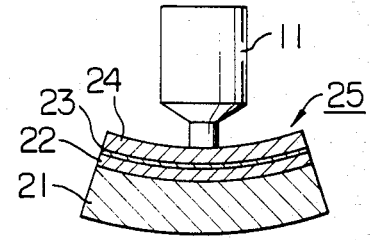
FIG. 7 is a partially sectional view showing a cast structure secured to a curved test piece of a plain bearing.

Referring now to FIG. 7, there is shown a cast structure 11 attached to a test piece 25 which is curved in configuration and includes a steel backing layer 21, a copper-lead alloy layer 22, a nickel plating layer 23 and a lead alloy surface layer 24. The present invention can naturally be applied to such curved test pieces. In constructing such an assembly as shown in FIG. 7, soft solder would flow out of the lower end of a mold 10 unless the edge of a small diameter opening of the mold 10 conformed to the curved surface of the lead alloy surface layer 24. Therefore it is necessary to take some suitable measures for coping with such requirements.

Figure 8:
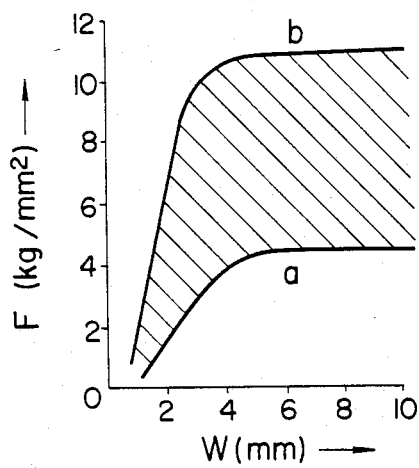
FIG. 8 is a graph showing a relationship between the thickness of a multi-layer material and the adhesive strength thereof as measured.

Referring now to FIG. 8, a change in a tensile strength F (kg/mm$^2$) as measured is shown when the thickness W (mm) of the same multi-layer material as shown in FIG. 1 is varied. In the drawing, the upper and lower limits of the measurements of tensile strength are represented by b and a, respectively. As seen from FIG. 8, substantially accurate measurements of tensile strength can be obtained directly when the thickness of the test piece is more than 4 mm. However, the present invention can be also applied in the case of thin test pieces by effecting a compensation for width and other factors employing information; such as that shown in FIG. 8.

Figure 18:
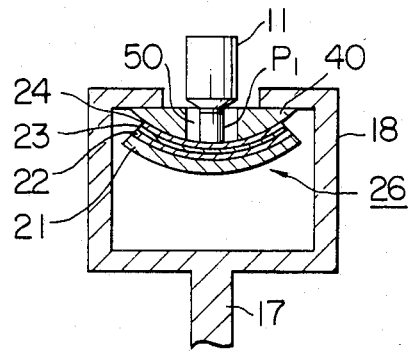
FIG. 18 is a fragmentary sectional view showing a test piece mounted on a holder.

In order to acurately measure the adhesive strength of the test piece without compensation by the use of such factors, however, supplementary tools 40, 41, 42 and 43 as shown in FIGS. 12 through 17 may be suitably selected and used in measurement of tensile strength which tools have different curvatures corresponding to the curvature of a thin test piece 26 (FIG. 18). The curvature of the supplementary tool to be used must be equal to or slightly smaller than that of the inner diameter of the test piece. This is because it is essential to avoid concentration of forces on the end of the test piece 26 during the tension test. The supplementary tool 40 is shown in plane in FIG. 12 and in section along the lines XIII—XIII and XIV—XIV in FIGS. 13 and 14, respectively. Other supplementary tools 41, 42 and 43 having different curvatures from that of the supplementary tool 40 are shown in section in FIGS. 15 through 17. Reference numeral 50 in FIGS. 12 through 18 designates a through hole of a slightly larger diameter than that of the cast structure 11 so as to enable inserting the same therethrough.

FIG. 18 shows a manner in which a test piece 26 having a thickness of 4 mm or below is mounted on the holder 18. As the supplementary tool 40 having the through hole 50 is used in measurement of tensile strength, tensile load uniformly exerts on the entire curved surface of the test piece 26 to provide substantially true values as shown in TABLE 1. As apparent from FIG. 19, a curve a represents a lower limit of measurements conventionally obtained without the use of the supplementary tool 40 and a curve $a_1$ represents the case in which the supplementary tool is used. In the drawing, a curve b represents an upper limit of measurements conventionally obtained without the use of the supplementary tool 40 while a curve $b_1$ represents the case in which the supplementary tool is used. Thus substantially true values can be obtained when the supplementary tool is used. In other words, the supplementary tools 40 to 43 having curvatures equal to or smaller than that of thin test pieces having a thickness of 4 mm and below have not been used in prior measuring methods when tensile strength of such test pieces is measured, so that measurement is greatly influenced by the force acting on the end of the test piece which force is produced due to flexure of the test piece 26 to provide measurements of adhesive strength smaller than the true values.

TABLE 1

| Thickness of test pieces | 1.5 | 2.0 | 3.0 | 4.0 | Note |
|---|---|---|---|---|---|
| Supplementary tools are not used | 2.8 kg/mm² | 4.3 kg/mm² | 9.4 kg/mm² | 9.8 kg/mm² | Correction is needed |
| Supplementary tools are used | 5.0 kg/mm² | 6.4 kg/mm² | 9.5 kg/mm² | 10.0 kg/mm² | Correction is not needed |

Figure 20:
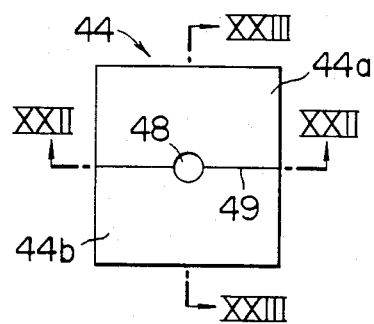
FIG. 20 is a plan view showing a supplementary tool having two halves.
Figure 21:
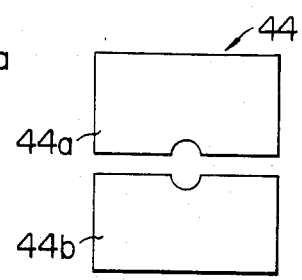
FIG. 21 is a plan view showing two halves of the supplementary tool of FIG. 20.
Figure 24:
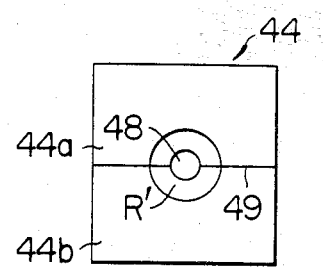
FIG. 24 is a bottom view showing the supplementary tool of FIG. 20.
Figure 22:
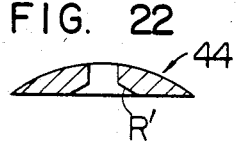
FIG. 22 is a sectional view taken along the line XXII—XXII in FIG. 20.
Figure 23:
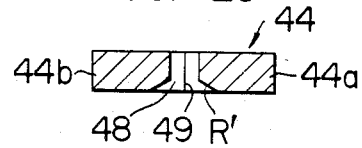
FIG. 23 is a sectional view taken along the line XXIII—XXIII in FIG. 20.

All the supplementary tools 40 to 43 each having the through hole 50, as shown in FIGS. 12 to 18 are formed of a solid material. As shown in FIG. 18, there is provided an air gap between the outer periphery of the first column portion $P_1$ of the test piece 26 and the inner periphery of the through hole 50. Due to the existence of such gap, more specifically due to the concentration of load at the contact area between the edge of the through hole 50 and the curved surface of the test piece 26, there is disadvantage in that true values can not be obtained in measurement of adhesive strength. Split-type supplementary tools 44, 45, 46 and 47, as shown in FIGS. 20 to 28, are helpful in obviating such disadvantage. The split-type supplementary tool 44, as shown in FIGS. 20 and 24, is formed of two halves 44a and 44b, as shown in FIG. 21.

FIG. 20 shows the supplementary tool 44 which is formed by combining the two halves 44a and 44b, and reference numeral 48 designates a through hole having a diameter equal to or slightly larger than the diameter of the first column portion $P_1$ of the cast structure 11. Reference numeral 49 designates a seam between the two halves 44a and 44b.

Figure 25:
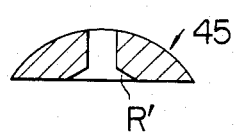
FIGS. 25 to 27 are sectional views showing a split-type supplementary tool having a different curvature from that of the supplementary tool of FIG. 20.
Figure 26:
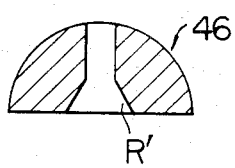
Figure 27:
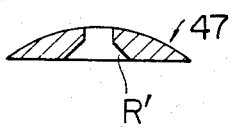

In FIGS. 25 to 27, there are shown other split-type supplementary tools 45, 46 and 47 adapted to be used when the curvature of the test piece and the length of the first column portion $P_1$ are different from those with the case of FIGS. 20 to 24.

Character R' designates a portion of the respective split-type supplementary tools, which is adapted to contact with the frustoconical portion R of the cast structure 11.

Figure 28:
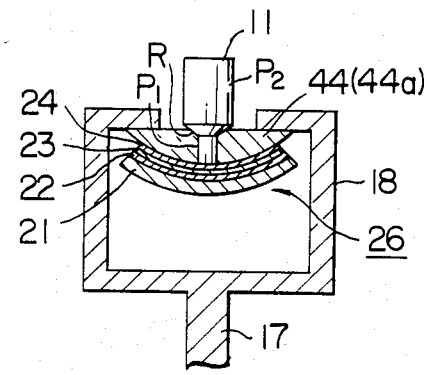
FIG. 28 is a fragmentary sectional view showing a test piece mounted on a holder with a split-type supplementary tool therebetween.

FIG. 28 shows a manner in which a test piece 26 having a thickness of 4 mm and below is mounted in the holder 18. The use of the supplementary tool 44 obviates the gap which is produced adjacent the through hole 50 of the supplementary tool 40 as shown in FIG. 18, so that the first column portion $P_1$ is always placed in engagement with the split-type supplementary tool 44 to cause tensile load to uniformly exert on the entire curved surface of the test piece 26 in measurement of adhesive strength, thus providing substantially true values as represented in TABLE 2.

Figure 29:
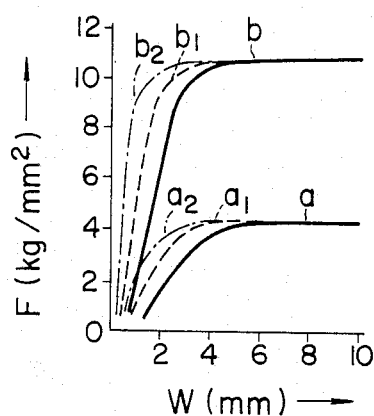
FIG. 29 is a graph showing measurements obtained with and without a gap between the first column portion of a test piece and the supplementary tool.

As seen from FIG. 29, nearly true values can be obtained in the measuring method in which the first column portion $P_1$ of the cast structure 11 engages with the supplementary tool 44 rather than in the measuring method in which there is produced a gap between the first column portion $P_1$ and the supplementary tool 40.

More specifically, the curve $a_1$ representing the lower limit of the measurements obtained with the supplementary tool 40 is displaced laterally to provide a newly corrected curve $a_2$, and the curve $b_1$ representing the upper limit of the measurements obtained with the supplementary tool 40 is also displaced laterally to provide a newly corrected curve $b_2$. In this manner, nearly true values of adhesive strength can be obtained.

TABLE 2

Figure 19:
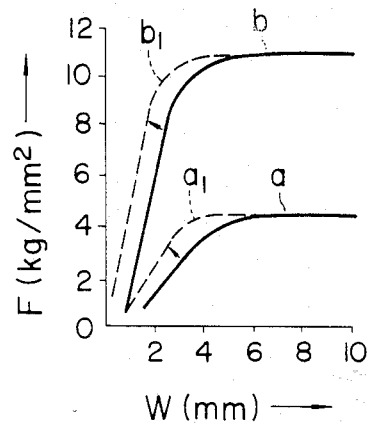
FIG. 19 is a graph showing measurements obtained with and without the use of a supplementary tool.

| Thickness of a test piece | 1.5 | 2.0 | 3.0 | 4.0 | Note |
|---|---|---|---|---|---|
| Supplementary tools (FIGS. 12 to 18) are used | 5.0 kg/mm² | 6.4 kg/mm² | 9.5 kg/mm² | 10.0 kg/mm² | Reference is made to FIG. 19. |
| Supplementary tools (FIGS. 20 to 27) are used | 8.1 kg/mm² | 9.4 kg/mm² | 9.8 kg/mm² | 10.1 kg/mm² | |

As described above, adhesive strength of a four-layer material, that is, close adhesion between a plating layer and a bearing alloy layer or between the plating layer and a surface layer is measured. However, the present invention is not limited to such case of four-layer materials but can be applied to measurement of an adhesive strength between a steel backing layer and an adhesive layer of nickel or copper in a test piece which is sampled from a plain bearing having a steel backing layer, and an adhesive layer of nickel or copper in the course of manufacture.

Examples of such measurement are as follows:

(1) An adhesive strength between a copper-lead alloy layer and a nickel plating layer in the test piece as shown in FIG. 1 was approximately 4.0 to 5.4 kg/mm$^2$ which value was obtained by first measuring a tensile load 200 kg when the two layers were stripped from each other, and dividing the value of the tensile load by an area of the adhesive portion. The thickness of the test piece ranged from 3.9 mm to 8.2 mm.

(2) A test piece constructed in the same manner as shown in FIG. 7 and having the same composition as shown in FIG. 1 was measured to provide a value substantially equal to the measurement as obtained in the above example.

(3) Measurement was conducted with respect to a test piece which was constructed in the same manner as shown in FIG. 7 and had substantially the same composition as that of the test piece of the example (2) except that the copper-lead alloy layer was replaced by an aluminum alloy layer of the composition as shown in the following Table 3 and the thickness of the test piece as used was in the range of 4.8 to 6.0 mm. As the result, the adhesive strength between the aluminum alloy layer and the nickel plating layer was found to be in the range of 1.5 to 5.4 kg/mm$^2$.

TABLE 3

| | (content %) | | | |
|---|---|---|---|---|
| | Sn | Cu | Ni | Al |
| 1 | 17.5–22.5 | 0.7–1.3 | less than 0.15 | the remainder |
| 2 | 35.0–42.0 | 0.7–1.3 | less than 0.15 | the remainder |
| 3 | 45.0–65.0 | 0.1–1.5 | — | the remainder |

(4) Measurement was conducted with respect to a test piece which was constructed in the same manner as shown in FIG. 7 to have a thickness of 3.5 mm and had substantially the same composition as that of the test piece of the example (2) except that the copper-lead alloy layer and the nickel plating layer were replaced by an aluminum alloy layer and a copper plating layer, respectively. As the result, the adhesive strength between the aluminum alloy layer and the copper plating layer was found to have substantially the same value as in the example (3).

(5) Measurement was conducted with respect to a test piece which was constructed in the same manner as shown in FIG. 7 to have a thickness of 3.5 mm and had substantially the same composition as that of the test piece of the example (2) except that the copper-lead alloy layer and the nickel plating layer were replaced by an aluminum alloy layer and a titanium plating layer, respectively. As the result, the adhesive strength between the titanium plating layer and the aluminum alloy layer was found to have substantially the same value as in the example (3).

The present invention as described above has the following advantages:

First, test pieces can be cut from a material to be subject to measurement, which material may be a finished product or a semi-manufactured product in the course of manufacture. Accordingly, it is possible to measure an adhesive strength between desired layers of a test piece as well as between a layer of the least adhesive strength and other layers in a multi-layer material.

Also, an adhesive strength can be quantitatively measured to provide a correct value since test pieces are cut from actual products, as desired. In case test pieces must be prepared separately, it is doubtful whether the adhesive strength associated with such test pieces corresponds correctly to that associated with the actual products, which inconvenience can be avoided in the present invention.

Second, periods of time required for preparation of test pieces as well as for measurement of adhesive strength can be markedly reduced since test pieces may be in the form of a flat plate or a curved plain bearing.

Thirdly, the method according to the present invention is quite economical because a brazing metal such as soft solder can be melted for repeated use and test pieces can be readily prepared to reduce the cost of testing.

Since many changes and variations of the disclosed embodiment of the invention may be made without departing from the inventive concept, it is not intended to limit the invention otherwise than as required by the appended claims.

What is claimed is:

1. A method for measuring adhesive strength of a multi-layer material, said method comprising:
   placing a mold on one surface of said multi-layer material to be tested;
   casting a brazing metal into said mold to form and secure a resulting cast structure to said one surface of the multi-layer material, said structure including a first column portion connected to and extending substantially upright from said one surface, an intermediate portion extending upright from the upper end of said first column portion and diverging upward in diameter, and a second column portion extending from the upper end of said intermediate portion;
   selecting said first column portion to have a length sufficiently small to prevent breakage thereof while measuring the adhesive strength of said multi-layer material
   causing one of a pair of chucks of a tension tester to grasp said second column portion of the cast structure and the other of said chucks to grasp said multi-layer material or a holder adapted for mounting therein said multi-layer material; and
   applying a tensile force to the respective layers of said multi-layer material in a direction transverse to said layers.

2. A method as set forth in claim 1 wherein a surface layer of said multi-layer material has a thickness of more than 0.1 mm and wherein a notch portion is formed circumferentially about said first column portion into said surface layer and a layer immediately below the surface layer.

3. A method as set forth in claim 1 wherein the other of said chucks grasp a holder and a supplementary tool is interposed between said one surface of the multi-layer material and said holder, which supplementary tool has curved surface of a curvature corresponding to that of said one surface of the multi-layer material.

\* \* \* \* \*